(12) United States Patent
Alt

(10) Patent No.: US 6,398,805 B1
(45) Date of Patent: Jun. 4, 2002

(54) BALLOON EXPANDABLE STENT WITH LOW SURFACE FRICTION

(75) Inventor: Eckhard Alt, Ottobrunn (DE)

(73) Assignee: Inflow Dynamics Inc., Wilmington, DE (US)

( * ) Notice: Subject to any disclaimer, the term of this patent is extended or adjusted under 35 U.S.C. 154(b) by 0 days.

(21) Appl. No.: 09/544,780

(22) Filed: Apr. 7, 2000

Related U.S. Application Data

(63) Continuation-in-part of application No. 08/933,627, filed on Sep. 19, 1997, now abandoned, which is a continuation-in-part of application No. 08/904,788, filed on Aug. 1, 1997, now Pat. No. 5,855,600.

(51) Int. Cl.$^7$ .................................................. A61F 2/06
(52) U.S. Cl. .................................................. 623/1.15
(58) Field of Search ............................. 623/1.15, 1.16; 600/198

(56) References Cited

U.S. PATENT DOCUMENTS

| | | | | |
|---|---|---|---|---|
| 5,630,829 A | * | 5/1997 | Lauterjung | 606/198 |
| 5,810,872 A | * | 9/1998 | Kanesaka et al. | 606/198 |
| 5,817,152 A | * | 10/1998 | Birdsall et al. | 623/1.15 |
| 5,827,321 A | * | 10/1998 | Roubin et al. | 606/195 |
| 5,925,061 A | * | 7/1999 | Ogi et al. | 606/198 |
| 5,980,553 A | * | 11/1999 | Gray et al. | 606/198 |
| 6,203,569 B1 | * | 3/2001 | Wijay | 623/1.15 |
| 6,258,116 B1 | * | 7/2001 | Hojeibane | 623/1.16 |
| 6,331,189 B1 | * | 12/2001 | Wolinsky et al. | 623/1.15 |

* cited by examiner

Primary Examiner—David H. Willse
Assistant Examiner—Suzette J. Jackson

(57) ABSTRACT

A vascular or endoluminal stent has low surface friction for ease of navigating a vessel, duct or tract of a patient. The stent is configured as a tubular element of biocompatible material having a longitudinal axis, open ends and a multiplicity of openings of generally common shape and size through its wall throughout its length. The openings are bounded by a network of tangentially interconnected, continuous, predominantly longitudinally oriented curvilinear struts, without discontinuity, forming a sidewall of the tubular element. The stent is adapted to be deployed by exertion of outward radial pressure on the tubular element, and when deployed, at least a segment of each strut undergoes a transition to a predominantly transverse orientation relative to the longitudinal axis of the stent.

25 Claims, 6 Drawing Sheets

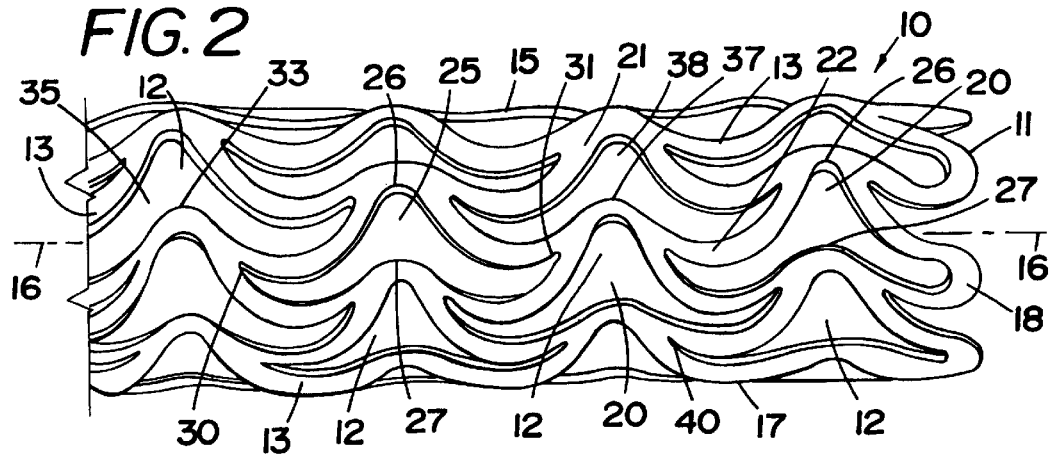
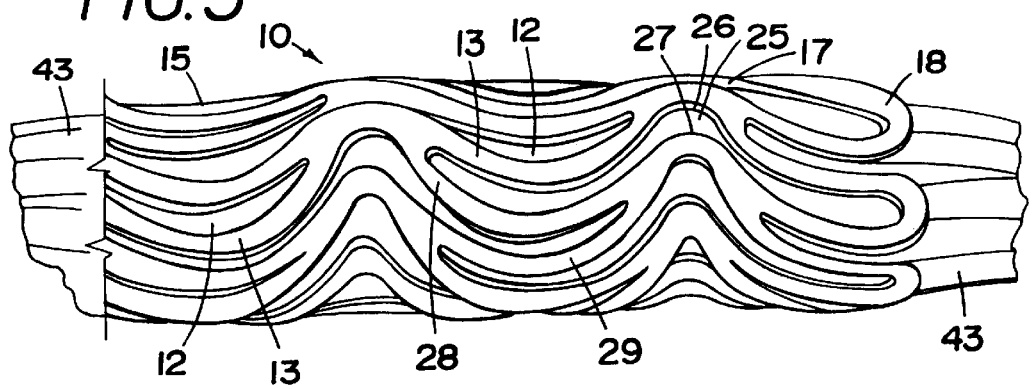
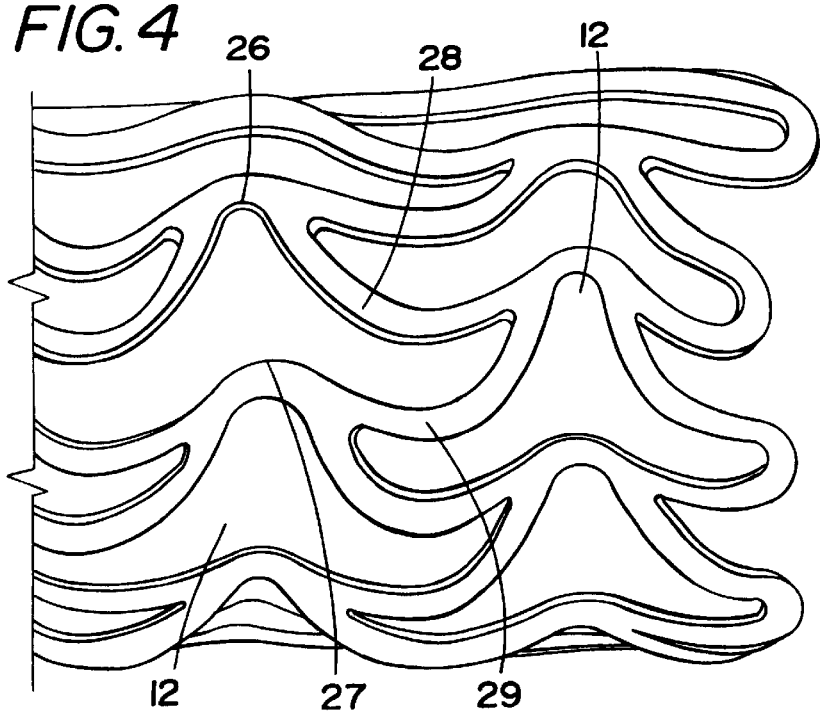

BALLOON EXPANDABLE STENT WITH LOW SURFACE FRICTION

CROSS-REFERENCE TO RELATED APPLICATIONS

This application is a continuation-in-part of applicant's U.S. patent application Ser. No. 08/933,627, abandoned filed Sep. 19, 1997, which is a continuation-in-part of applicant's U.S. patent application Ser. No. 08/904,788, filed Aug. 1, 1997, now U.S. Pat. No. 5,855,600, issued Jan. 5, 1999 ("the '600 patent"), each assigned to the same assignee as the present application.

BACKGROUND OF THE INVENTION

The present invention relates generally to stents which are implantable or deployable in a vessel or duct within the body of a patient to maintain the lumen of the duct or vessel open, and more particularly to an improved highly flexible, low friction stent structure.

Stents are implantable by deployment in a vessel or duct within the body of a patient to maintain the patency (unblocked or unclogged characteristic) of the lumen of the duct or vessel; i.e., to keep the vessel open. The stent itself is a tubular, perforated wall, open-ended, expandable vascular or endoluminal prosthesis. Although it has enjoyed widespread use principally to keep a designated target site of the lumen in a blood vessel open and unoccluded, especially in the coronary and femoral arteries following angioplasty, the device has found increasing use for the same or similar purpose in other places in the human body. Examples include maintaining the lumen open and unobstructed at a preselected target site in the tracheobronchial system, the biliary hepatic system, the esophageal bowel system, or the urinary tract system.

A vascular stent, in particular, must be of sufficient dimensional stability to keep the lumen of the vessel open while resisting recoil of its elastic wall that naturally occurs when the target site within the vessel or luminal structure has been subjected to outwardly directed forces necessary to expand the elastic fibers during deployment of the stent. It was found that a large percentage of patients who had undergone an angioplasty procedure were returning with blockage of the same coronary artery within three to six months after the angioplasty was performed. It was subsequently discovered that the new blockage was attributable to a different mechanism—the trauma to the artery wall during the angioplasty procedure had caused a proliferation of smooth muscle cells (hyperplasia) which constituted restenosis—in this case somewhat akin to scarring. Implantation of a coronary stent can serve not only to reduce acute complications following an angioplasty intervention, but also improve the long term outcome, such as to inhibit restenosis and suppress or limit recoil by the stent's scaffolding and support of the vessel wall.

Among the different stent designs are a wire mesh type, a coil type with a helical wire configuration, a slotted tube type, and a multicellular type which is a modification of the slotted tube type with less surface coverage and smaller openings. Typically, the stent is implanted from a delivery system which includes a catheter, a balloon generally at or near the distal end of the catheter, and an inflation lumen in the catheter for selectively inflating and deflating the balloon with a suitable biologically compatible fluid, the stent being crimped onto the balloon. The balloon catheter with stent must, of course, have a diameter smaller than the diameter of the vessel in which the stent is to be implanted. A coronary artery may have a diameter of only about 3 millimeters. The catheter is inserted from its proximal end into the vessel and advanced until the stent is aligned (as viewed under fluoroscope by the implanting physician) at the target site, such as a section of a coronary artery which has just been treated with an angioplasty procedure, and the stent is then deployed by inflating the balloon to expand the stent diameter, whereby the stent engages and at least slightly expands the lumen diameter of the vessel wall.

In addition to adequate support strength in the deployed state—sometimes referred to as mechanical scaffolding, hoop strength or radial strength—to resist vessel wall recoil and to maintain the vessel patency, the stent also must be sufficiently flexible to be advanced through the lumen of an often narrow and tortuous vessel on its delivery system catheter without injuring or distending the vessel wall. Indeed, the stent must have a capacity to resist and yet flex with the repetitive pressures exerted on it by the coronary artery wall according to the systole and diastole of a beating heart. It is therefore necessary that some compromise be reached between these two conflicting requirements. The '600 patent discloses a composite stent design pattern of interconnected struts and openings therebetween in the stent's tubular wall which is different along its mid-section from either of its end segments, giving the stent greater rigidity at its mid-section and greater flexibility at its ends. The more rigid mid-section can better withstand recoil and repetitive pressure of the vessel wall when the stent is deployed. The more flexible ends allow the undeployed (crimped, or compressed) stent to better traverse tortuous paths encountered during advancement through the lumen of the vessel, and the deployed stent to accommodate repetitive wall flexation. Also, the more flexible ends provide a smooth transition between the native vessel wall and the more rigid mid-section, so as to match the biomechanics of the vessel itself A coronary (vascular) stent must be implanted rapidly, to avoid the possibility of subjecting the patient to risk of myocardial infarction owing to the reduction or even complete blockage of blood flow through the coronary artery while the stent delivery system is being navigated through the vascular system and ultimately deployed at the target site. This imposes even greater importance on axial or longitudinal flexibility of the stent, as well as the skill of the implanting physician. Additionally, it is crucial that the stent exhibit low surface friction. Many of the body vessels, tracts or ducts through which a stent must be advanced to reach the target site exhibit a surface which is not smooth, but rather, uneven, calcified or stenosed.

Therefore, an ideal stent must be structured to minimize the impact of surface friction along the path it must traverse, as well as possess features of longitudinal flexibility and mechanical scaffolding. Low surface friction is especially important in the compressed state or condition of the stent when it is mounted on the balloon catheter of the delivery system, for it is in this condition that the stent must be guided through the vessel. It is unacceptable for the stent structure itself to exacerbate the problem of friction along the path, by presenting a compressed state whose surface friction characteristics, coupled with longitudinal bending of the stent that must take place during advancement through a curved vessel, creates hook-like anomalies at the outer surface of the stent.

It is a principal aim of the present invention to provide a stent having structural characteristics of high longitudinal flexibility, strong mechanical scaffolding, and low surface friction, compared to previous stent designs.

In heretofore available stent designs, whether of the mesh, coil, slotted or multicellular type, it has been customary to provide transversely or laterally oriented structural elements (relative to the longitudinal axis of the stent) that interconnect longitudinally oriented elements in the stent structure. An extreme example is the coil stent, in which a single element (the coil itself) provides both longitudinal and transverse orientation relative to the direction of advancement of the stent through the vessel or duct. Transverse elements or portions of a stent structure tend to exacerbate surface friction during advancement (or withdrawal) of the stent through the vessel, particularly if the stent undergoes longitudinal bending as it traverses a tortuous vessel. In general, bending becomes more pronounced as stent length increases.

Therefore, another aim of the present invention is to provide a stent structure of the slotted tube or multicellular type in which the structural elements are oriented or aligned in a predominantly (i.e., virtually entirely) longitudinal direction relative to the axis of the stent.

An additional factor which makes stent structural elements of predominantly longitudinal orientation a functionally desirable design is that the stent is more readily compressed onto the uninflated balloon of the delivery system with a small profile. Presently available catheter-mounted balloons offer a minimum uninflated diameter in the range from about 0.6 to 0.7 millimeters, which dictates a minimum circumference of about 2.0 mm. A stent compressed onto the balloon should not measurably increase that minimum circumference, so the compressed stent preferably should not exceed a circumference of about 2.0 mm. This tends to assure passage of the stent through a small diameter coronary artery, prevention against the stent being dislodged from the balloon as the catheter is advanced to the target site in the artery. Transversely oriented structural elements much more profoundly limit the extent to which the stent may be compressed as it is crimped onto a low profile balloon, than do longitudinally oriented structural elements.

Accordingly, another objective of the invention is to provide a stent with optimum longitudinal orientation of all its structural elements, to permit the stent to be compressed to a diameter of less than 1.0 mm onto a delivery balloon, and to reduce the surface friction characteristics of the stent for more rapid advancement through a narrow diameter vessel.

SUMMARY OF THE INVENTION

Briefly, according to the invention the stent has the customary generally cylindrical, open-ended, tubular structure with a longitudinal axis, but in its production (i.e., completed manufacture) state, as well as its radially compressed state or even its partly expanded (i.e., pre-opened) state, has a self-supporting latticework sidewall with predominantly longitudinally oriented elements (struts, links or strips). Each of these interconnected struts has the predominantly longitudinal orientation relative to the axis of the stent, with none having a predominantly transverse orientation relative to that axis. The effect of this design of the latticework sidewall is to optimize its outer surface for low friction when the stent is being advanced or withdrawn through the duct or vessel to or from a target site.

The sidewall is of generally uniform thickness, with a multiplicity of holes therethrough that enable the stent to be selectively expanded radially during inflation of the delivery balloon when the stent is being deployed. In its expanded state, in which the stent is adapted to engage the wall of the vessel at the target site, a considerable number of the struts in the sidewall are deformed, during stent deployment and by virtue of the structural design and composition of the stent, from the longitudinal orientation to a transverse orientation that provides a self-supporting, mechanical scaffolding sufficient to resist radial compression under forces exerted by recoil of the vessel wall and ongoing repetitive flexing in the case of a blood vessel.

In a presently preferred embodiment, a vascular or endoluminal stent comprises a biocompatible hollow tube having a longitudinal axis and open ends, a multiplicity of openings through the wall of the tube between the ends, the stent having a production state, a second state in which the stent is radially compressed and a third state in which the stent is radially expanded relative to the production state. The stent is adapted for deployment to its expanded state in a vessel, duct or tract of a patient. The multiplicity of openings through the wall of the tube is defined when the stent is in the production state by a network of tangentially interconnected, solely curvilinear struts, each of the struts running longitudinally from end to end of the tube in repetitively alternating crests and valleys without sharp breaks or angularity.

Each of the openings is bounded circumferentially on the tube by an upper curve and a lower curve connected to form a closed curve. One of these upper and lower curves has a tighter curvature than the other. As viewed in one aspect, each opening in the wall of the stent has a shape resembling the outline of a ram's head with horns projecting outwardly and upwardly at sides of the head. In this aspect, each of the upper and lower curves of each opening has a single valley or trough. As viewed in another aspect, each opening in the wall of the stent has a shape resembling the outline of a handlebar moustache or a Dutch winged cap. In that aspect, each of the upper and lower curves of each opening has a single crest.

In either case, no segment of any strut is oriented in a direction generally perpendicular to the longitudinal axis when the stent is in either its production state or its compressed state. But when deployed to the expanded state, each strut has at least one segment oriented in a direction generally perpendicular to the longitudinal axis. The tube that forms the stent is longitudinally flexible to undergo a bend defining an inner arc and an outer arc, wherein the openings closest to the inner arc have upper and lower curves closer together than the upper and lower curves of circumferentially aligned openings closest to the outer arc.

The stent is composed of a material such that the circumferentially aligned openings in the tube wall from the inner arc to the outer arc will undergo recovery toward their respective original configurations upon straightening of the bend, when the bend has occurred with the stent in its compressed state as would be the case during navigation of the stent (mounted on its delivery system) through a curved vessel. However, when the bend is an accommodation to a curve at the target site during deployment of the stent to its expanded state, the material undergoes plastic deformation such that the circumferentially aligned openings in the tube wall from the inner arc to the outer arc will remain in respective configurations of upper and lower curves being closer together or further apart according to their closeness to the inner arc or outer arc, respectively.

BRIEF DESCRIPTION OF THE DRAWINGS

The above and still further aims, objects, features, aspects and attendant advantages of the invention will become apparent from the following description of a preferred embodiment and manufacturing method, constituting the best mode presently contemplated of practicing the invention, when taken in conjunction with the accompanying drawings, in which:

FIGS. 2, 3, 4 and 5 are each a partial or fragmentary side view in perspective of the preferred embodiment of the tubular stent having the latticework or network design of FIG. 1, in the production state, compressed condition, partially opened condition, and completely opened condition, respectively, and in which FIGS. 4 and 5 are of higher magnification or larger scale than FIGS. 2 and 3, and the compressed stent of FIG. 3 is mounted on a balloon for implantation in a patient;

DETAILED DESCRIPTION OF THE PRESENTLY PREFERRED AND ALTERNATIVE EMBODIMENTS AND METHODS

It should be noted that the Figures of drawing are not to scale. Where appropriate the representations are simplified or fragmentary, such as by omitting structural detail of the far side of the stent which would be observable through openings on the near side (as viewed in the Figure) to avoid unnecessary clutter and obscuration; and in some instances by supplying relatively complete detail of only a part of the stent design although it will be understood that the same pattern would be present throughout. Also, a Figure or portion thereof may be of highly exaggerated scale for emphasis. The same reference numbers are used throughout the Figures to designate the same elements.

Figure 1:
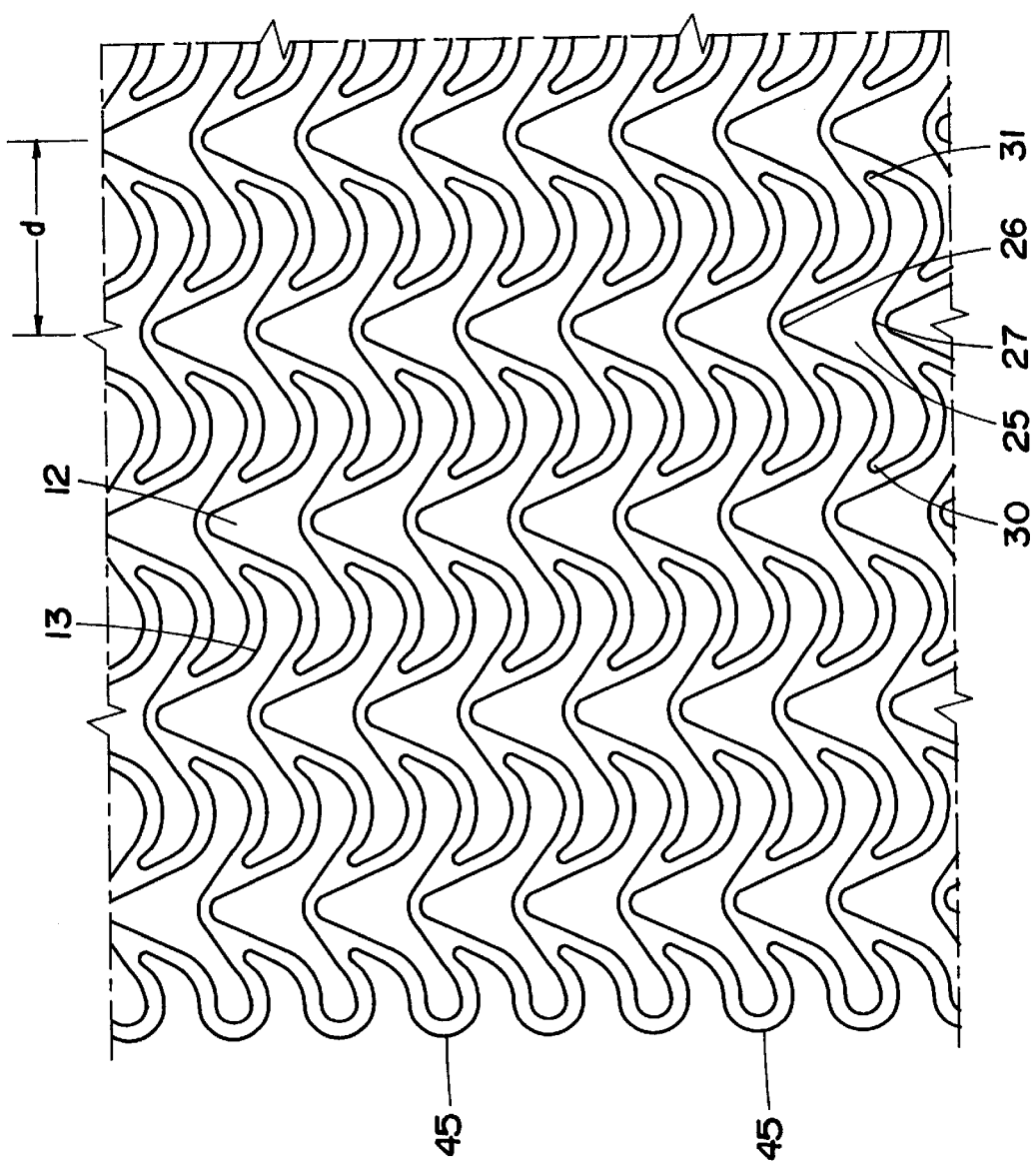
FIG. 1 is a partial or fragmentary plan (flat) view of the design of the latticework or network of links or struts in the sidewall of a preferred embodiment of a stent according to the present invention, in a production or pre-opened state.
Figure 5:
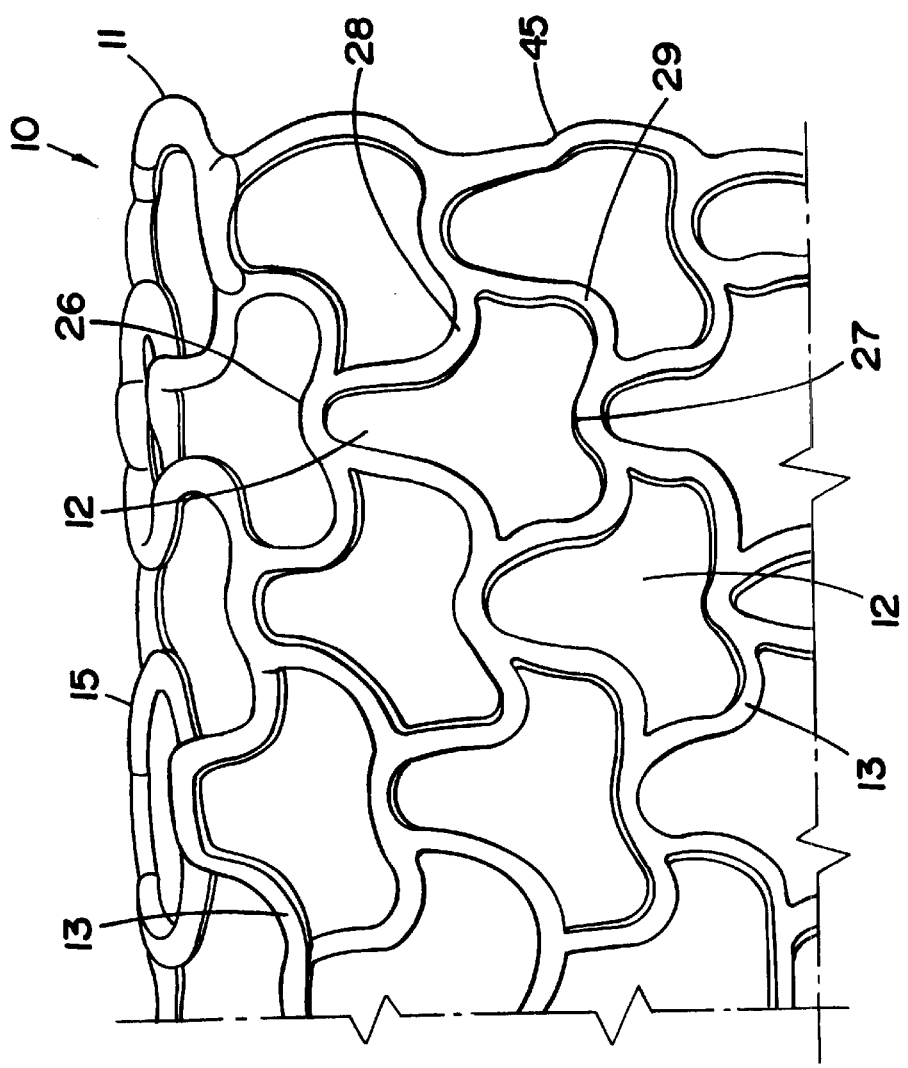

A preferred multicellular stent design is depicted in plan or flat view in FIG. 1, in the production or completed manufacture state. This is the state in which the stent, if in its tubular configuration, would be supplied for implantation by physicians at a medical center. Although described for illustrative purposes in preferred and alternative embodiments as a vascular stent, it may be used to provide wall support in various vessels, ducts or tracts of the human body.

The stent 10 (FIG. 2, which is a side view in perspective of the production state) comprises an open-ended tube, tubular member or generally cylindrical member 11 composed of metallic material biocompatible with the tissue and blood of the human body. Tube 11 may, for example, have a diameter of 1.6 mm, a length of 15 mm, and a wall thickness in the range from 50 to 80 microns (micrometers, or $\mu$m). Tube 11 has a sidewall 15 with a multiplicity of through-holes, apertures or openings 12 through it, defined and bounded by a plurality of curvilinear struts, strips or links 13. The struts are cut out to form a network or latticework sidewall, such as by use of a narrow laser beam of a conventional laser cutter following a programmable pattern. The removed material from openings 12 is discarded.

According to the invention, the resulting pattern in the latticework sidewall 15 is a network of interconnected curvilinear struts 13, each of which runs the entire length of the tube or stent, and is predominantly longitudinally oriented relative to axis 16 of tube 11, without any discontinuity, sharp breaks or sharp angularity. None of the struts is oriented generally perpendicular to axis 16. Consequently, the outer surface 17 of the stent 10 exhibits a substantially reduced frictional characteristic compared to stents of the prior art, thereby better avoiding interference with or injury to the vessel wall as it is advanced to a preselected target site for deployment.

In the preferred embodiment, the stent's network of curvilinear struts 13 defines a series or sequence of longitudinally repeating circumferential rows 20 of openings or cells 12, in which each opening has a shape which resembles the outline of a handlebar moustache, or of a Dutch winged cap, viewed as shown in the Figures (perhaps most prominent in FIGS. 1 and 2). Each opening is bounded by struts constituting alternating links in wavelets of higher and lower crests in successive rows of each circumferential column displaced along the length of the cylindrical element. The curvilinear struts may also be characterized as a sequence of tangentially interconnected repetitive crests that alternate between low crests 33 and high crests 26 (FIG. 2) that define the shape of the cells or openings.

Figure 7:
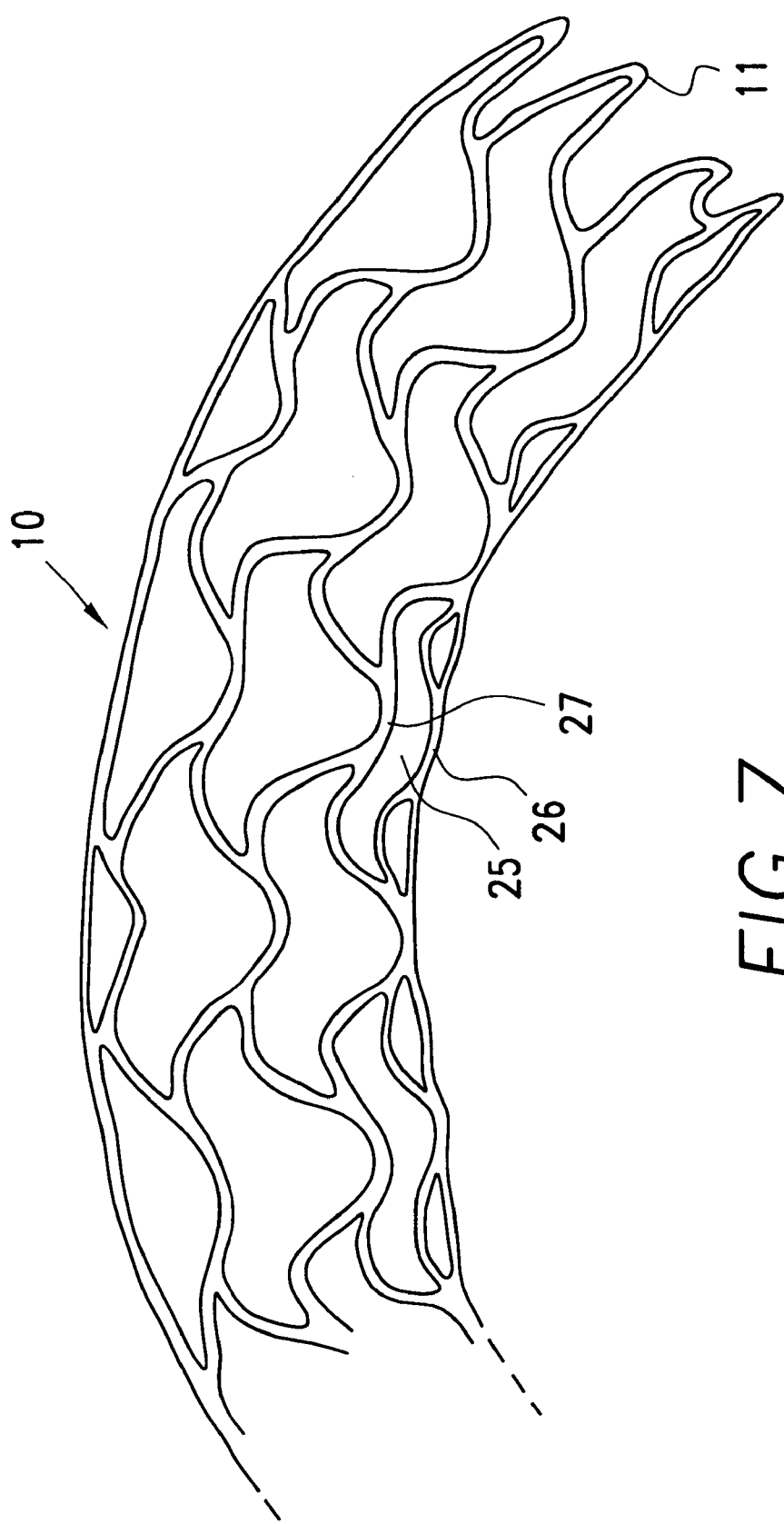
FIG. 7 is a partial or fragmentary side view of a stent of the preferred embodiment in its production state, in a curved or bent condition.

As shown in FIG. 7, or if the other Figures are turned upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element. It is noteworthy that each structural element or strut continues its curvilinear excursion from one end to the other end of the stent throughout.

More specifically, as viewed in the upright Figures, each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at least at one side of the crests, and preferably at each side (30, 31) thereof It will be observed from FIG. 2 that the intersection 30 of struts at one side of the adjacent circumferentially aligned crests 26, 27 of row 25 is tangential to a crest 33 of the immediately adjacent row 35, and the intersection 31 of struts at the other side of those crests is tangential to a crest 37 of the immediately adjacent row 38.

Interconnecting points such as 40 between struts may be notched for symmetrical radial expansion of the stent during deployment thereof. Alternatively, as shown in FIG. 1, the interconnecting points may have fillets (rounds) to promote symmetrical expansion.

In an illustrative example of the embodiment of FIG. 1, assuming the aforementioned dimensions, the distance from the center of the crest of one row to the center of the crest of the immediately adjacent row (designated d) is 1.25 mm, which constitutes the length of a cell in this multicellular structure. For a 15 mm long stent, then, a total of twelve cells occupy this length. Nominally, the width of each strut lies in a range from 70 to 100 $\mu$m, with a maximum of sixteen longitudinally oriented struts in each circumferential row.

When stent 10 is crimped onto a small diameter delivery balloon 43 (FIG. 3), the adjacent circumferentially aligned crests such as 26, 27 of each row such as 25 move closer together. The pattern formed by the latticework of struts allows substantial nesting together of the crests and bows, and especially the struts such as 28, 29 when fully crimped (radially compressed), which assures a relatively small circumference of the stent in the crimped condition. With the dimensions specified above, the stent 10 may be crimped onto an uninflated balloon of only about 0.75 mm diameter. It will be observed that the use of predominantly longitudinally oriented struts, with no interconnecting strut lying substantially completely in an orientation transverse or perpendicular to the longitudinal axis of the stent, enables tight crimping of the stent on the low profile balloon, as well as decreasing surface friction of the stent during traversal of a vessel.

Computer simulations and in vitro and in vivo tests of the stent of FIGS. 2, 3, 4 and 5 have demonstrated that the stent is highly flexible, with the stent mounted on a balloon (FIG. 3) being capable of undergoing bending to a radius as small as one centimeter (cm) which corresponds to radii of particularly tortuous coronary arteries encountered in some individuals, without permanent plastic deformation. When the stent is bent in such a manner, the adjacent circumferentially aligned crests such as 26, 27 of a row such as 25, which have a slight gap between them when fully crimped, move even closer together along the inner arc of the bend and spread slightly further apart along the outer arc of the bend. This is shown in FIG. 7, and it will be observed that even though a foreshortening would normally be seen at the circumferentially curved upper and lower portions of the stent in the side view, FIG. 7 shows the closer nesting of crests (or troughs or valleys, in this depiction) at cells or openings in the vicinity of the inner arc and the greater separation between crests at cells or openings in the vicinity of the outer arc. While FIG. 7 depicts the stent in its production state, the same effect is achieved with the stent in the compressed state.

As the stent 10 is partially opened (FIG. 4) by inflation of the balloon (not shown in FIGS. 4 and 5, for the sake of clarity) during deployment, the adjacent crests 26, 27 begin to separate and the angle of division between struts 28, 29 begins to open. When the stent is fully expanded to a diameter of 3.5 mm, for example, the latticework of struts takes on the shape shown in FIG. 5, in which adjacent crests 26, 27 undergo wide separation, and segments of struts 28, 29 take on a transverse, almost fully perpendicular orientation relative to the longitudinal axis of the stent. The same occurs with segments of the struts 45 at each end of the stent, whereas in the initial production state (FIG. 1) those struts had been curled back on themselves between the dividing points at the respective side of the adjacent crests. This now-lateral orientation of a plurality of these strategically positioned struts is highly significant because each fully opened cell is now contributing to the firm mechanical support offered by the stent in its fully deployed condition, to assure a rigid structure which is highly resistant to recoil of the vessel wall following stent deployment.

It will be observed that the structural characteristics of stent 10 provide not only the desired compromise between flexibility of the device in its crimped state and rigidity of the device in its deployed (expanded) state, but serve the aims of the present invention by markedly reducing surface friction of the stent and enabling the stent to be crimped onto a very low profile balloon by virtue of the predominantly longitudinal orientation of the struts. Still further, the structural characteristics of this stent assure a highly symmetrical opening of the stent during deployment, without the twisting of struts and distortion of tubular shape that has characterized many of the prior art configurations.

A method of fabricating such a vascular or endoluminal stent according to the invention includes selecting as the starting material an open-ended tube of predetermined length composed of a biocompatible metallic material which may be a substantially pure single metal or an alloy conventionally used for such purposes. The tube has a self-supporting, relatively rigid sidewall of uniform thickness (e.g., dimensions of this and other aspects of the structure have been given by way of example above) that defines an outer diameter of the tube which is smaller than the diameter of the lumen of the vessel at the target site where the stent is to be deployed. Openings of the desired shape are formed in the sidewall of the tube by precise laser cutting according to a pattern programmed into the machine in a conventional manner. These openings render the sidewall flexible for bending easily about curves in the wall of the vessel as the stent is being inserted into the vascular system. The openings also allow the diameter of the tube lumen to be expanded to at least substantially the diameter of a fully open lumen of the vessel at the target site without tearing the sidewall, when a substantially uniform outwardly directed radial force of sufficient magnitude is exerted circumferentially along the entire length thereof by inflation of a delivery balloon on which the stent is mounted. At the same time, the self-supporting characteristic of the sidewall is maintained by the struts which assume a transverse orientation in the fully expanded condition of the stent.

Any burrs and sharp edges of the material are removed by an acid bath or further machining, and intersection points may be notched or rounded by further polishing to assure symmetrical opening of the device during deployment. The final structure may be heat treated (annealed) at an appropriate temperature to harden the metal or alloy of the stent.

In preparation for implantation, the stent is crimped onto a relaxed (deflated) expansion balloon of a balloon catheter of the delivery system, intermediate the ends of the balloon. The balloon itself is affixed at or near the distal end of the catheter, which has an inflation lumen (not shown). The balloon is then typically inflated to a pressure of from about 0.2 to 0.4 atmospheres, sufficient to distend its end portions that extend beyond the respective ends of the stent without substantially expanding the crimped stent thereon. In pre-mounting the stent on the balloon, i.e., prior to delivery of the system for implantation, the stent is crimped on the slightly longer inflation balloon while the balloon is under vacuum, after which the balloon is initially inflated to a pressure of from about 0.1 to about 0.5 (nominally, 0.2) atmospheres. The specific pressure selected is sufficient to partially inflate and slightly distend the balloon at its distal and proximal ends that extend beyond the ends of the stent, but insufficient to expand the diameter of the mounted stent. The slight inflation at the ends of the balloon serves to firmly center the stent, protect the stent from being dislodged, and avoid scraping the leading edge of the stent against the vessel wall during advancement to the selected site.

The stent 10 as crimped on a balloon 43 (FIG. 3) has a typical outer diameter of about 0.75 mm, which is achieved largely because of the absence of transverse bars or struts in the production state and, hence, in the compressed state which allows tight crimping onto a low profile balloon. Although stents generally are produced in lengths from about 5.0 to 25.0 mm, two "standard" lengths have been typically provided in the prior art, one standard length being fixed in a range from about 8.0 to 9.5 mm, and the other about 15.0 mm, for use with customary implantation balloon lengths of 10 mm and 20 mm.

After the stent has been advanced on the delivery system to the target site in the vessel, it is deployed by steadily increasing the inflation pressure of the balloon so as to expand the diameter (and thereby, the lumen opening) of the stent to a size appropriate for the vessel diameter. The typical diameter of a fully deployed (completely open) stent (FIG. 5) may range from about 2.5 to 6.0 mm, sufficient for firm retention of the stent in the vessel at the target site (e.g., the site of a lesion which has been subjected to an angioplasty intervention in a coronary artery). The stent may even be expanded to a point at which it is partly imbedded in the vessel wall, to provide a smooth continuous lumen to the flow of blood.

Figure 6A:
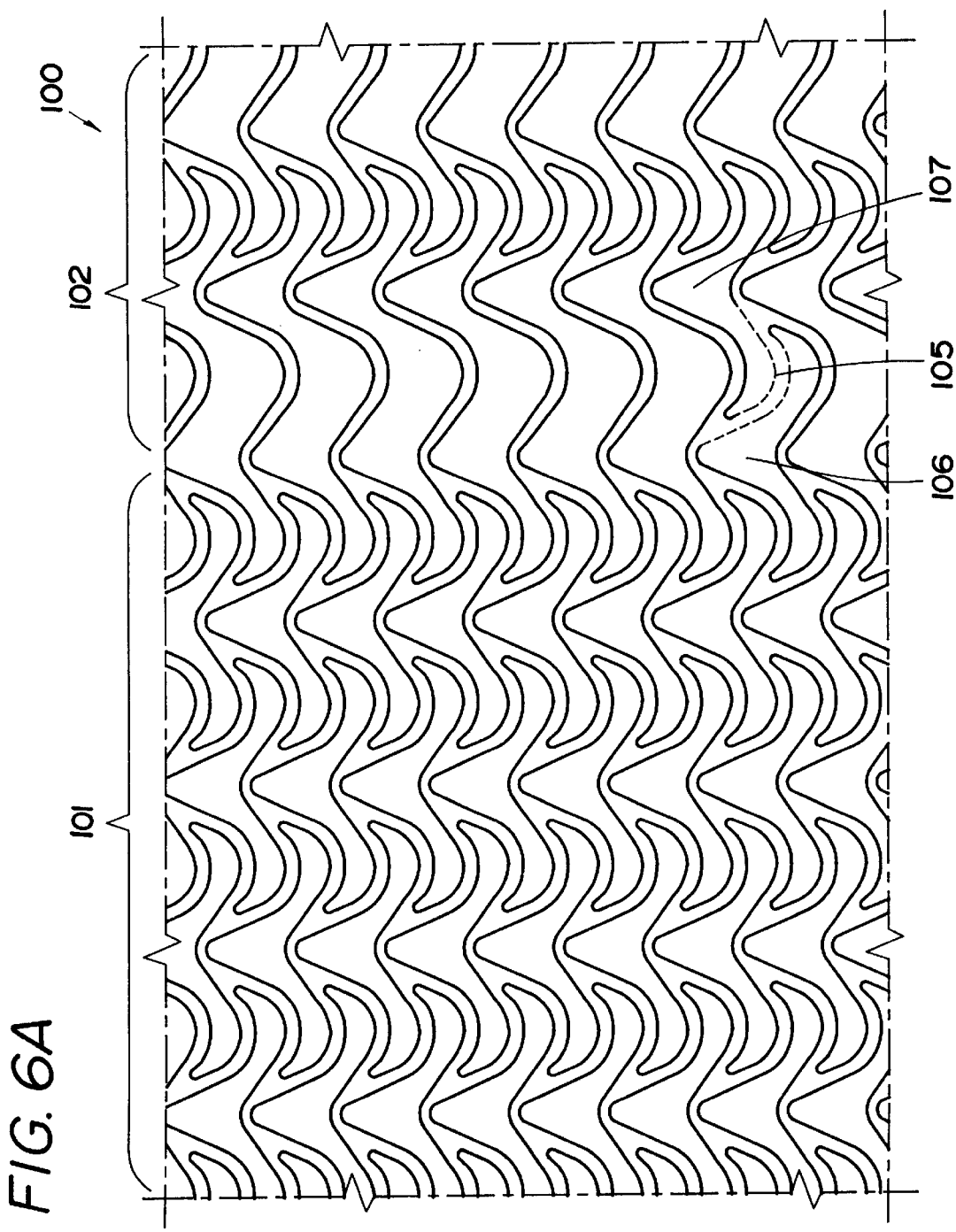
FIGS. 6A and 6B are partial or fragmentary plan (flat) views of alternative embodiments of the stent of the invention.
Figure 6B:
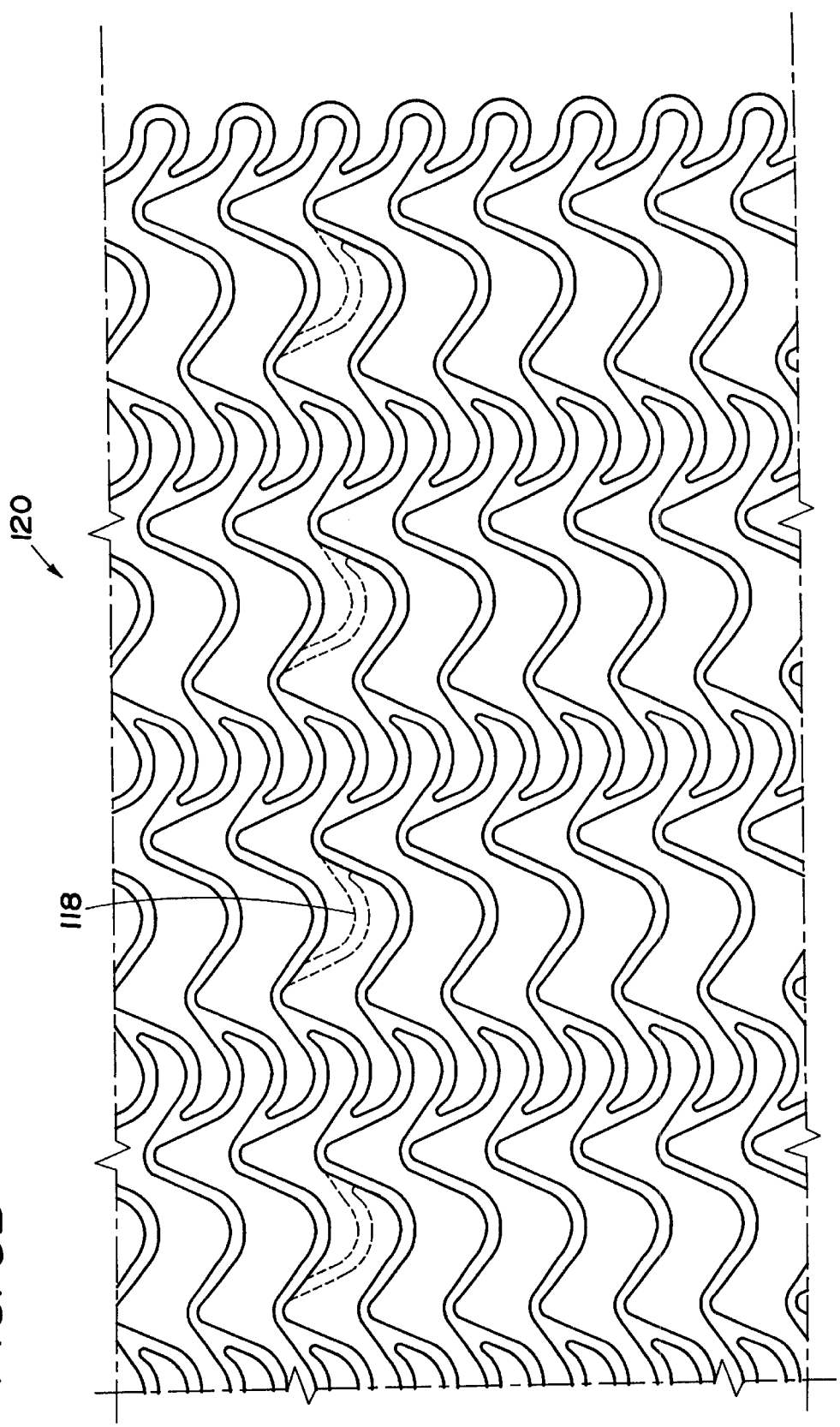

Alternative embodiments of stents using variations of the design described above are illustrated in the plan (flat) views of FIGS. 6A and 6B. In FIG. 6A, stent 100 is a composite of two slightly different designs, in which the central portion 101 has the design of FIG. 1, which offers flexibility with greater rigidity than portion 102. Only a part of the central portion and of one end portion are shown in FIG. 6A. Each of the end portions 102 of stent 100, which are identical, has a design which modifies the central portion 101 by omitting a strut as indicated at 105, and therefore provides a larger opening or cell between two adjacent rows 106 and 107 in circumferential columns at either side of the central portion 101. This is followed by a column and stacked rows in which the divided strut at one side of a crest (or trough) is maintained, and then another pair of adjacent rows lacking one of the divided struts. This composite design may be continued for additional rows depending on the desired length of the stent 100, and in any event, provides greater rigidity and, therefore, greater support of the vessel wall in the central portion 101, and somewhat greater flexibility in end portions 102.

In the alternative embodiment of FIG. 6B, the divider strut such as 118 is omitted from the structure at one side of the crest (or trough) of each wavelet in every other row of the structure of stent 120. In this composite design, the size of the openings or cells can be increased, for example, to a length of about 2.5 mm, so that a total of six cells can be provided end-to-end in a stent having a length of 15 mm. This embodiment has more flexibility throughout than the other embodiments, allows for even tighter crimping onto a delivery balloon, and tighter bending through curves in the vessel in which the stent is advanced, but less mechanical scaffolding. An alternating pattern of full individual cells and of cells with missing links such as 118 of FIG. 6B, achieves greater flexibility.

It will be observed that in each of the alternative embodiments, a strut is divided at only one side of each crest (or trough) in at least one row of a portion of the stent, to produce a pair of struts at that side, while the strut at the other side of each crest in that row extends through at least one additional crest of the immediately adjacent row before dividing into two struts.

From the foregoing description, it will be seen that the preferred embodiment provides a multicellular stent comprising a generally cylindrical open-ended metallic element having a longitudinal axis and a self-supporting latticework sidewall. The sidewall includes a multiplicity of cells in the form of openings of generally common sized and shape separated from one another by narrow curved strips extending generally in a predominantly longitudinal direction. Each of the cells has at least slightly different upper and lower curvatures of their respective strip boundaries to accommodate longitudinal bending of the stent. Each cell in the vicinity of the inner arc of a bend in the stent compresses from said common size to a smaller size with the curved strip boundaries thereof tending toward nesting together, while each cell in the vicinity of the outer arc expands to a larger size, to facilitate longitudinal bending.

The strips are patterned in the form of circumferentially-repeating wavelets extending continuously longitudinally from end to end of the element in alternating higher and lower crests connected tangentially to respective alternating lower and higher crests of adjacent wavelets, to facilitate relatively low friction longitudinal movement of the stent through a vessel, duct or tract of the patient's body. The stent has a radially compressed state of the cylindrical element for traversing the vessel to a deployment site, and a radially expanded state of deployment of the cylindrical element, and none of the strips is oriented in a plane perpendicular to the longitudinal axis of the cylindrical element when the stent is in its radially compressed state. Each of the strips has at least one segment oriented in a plane generally perpendicular to the longitudinal axis of the cylindrical element when the stent is in its radially expanded state, whereby to resist inwardly directed radial forces with greater rigidity than when the stent is in its radially compressed state.

Viewed somewhat differently, the stent comprises a biocompatible tubular member having a longitudinal axis and open ends, with a multiplicity of cells arranged in a regular pattern throughout the tubular member. Each cell constitutes an aperture in the wall of the tubular member. A plurality of curvilinear struts formed by narrow strips of the wall separate the cells from one another, each of the strips running the length of the tubular member in a continuously curvilinear manner without discontinuities. The strips have a sequence of tangentially interconnected crests that define the shape of the cells.

The sequence of tangentially interconnected crests alternates between circumferentially lower and higher crests in progression along the length of the tubular member, with tangential interconnection thereof to respectively higher and lower crests of corresponding adjacent ones of the sequences about the circumference of the tubular member. The cells are of generally uniform size and shape throughout the tubular member when the tubular member is in a generally straight longitudinal condition. The tubular member is adapted to undergo longitudinal bending during the traversal, and upon longitudinal bending the cells in the vicinity of the bend undergo a change in size, with circumferentially adjacent crests of the respective cell tending toward close nesting at the inner curvature of the bend and toward increased separation at the outer curvature of the bend. The cells return to their generally uniform size when the tube is straightened from the longitudinal bending.

The cells are generally symmetrical throughout the tubular member when the tubular member has a straight longitudinal axis. But when the tubular member is bent to have a curved longitudinal axis, cells in the vicinity of the bend undergo transition to an asymmetrical configuration without plastic deformation, thereby rendering the tubular member longitudinally flexible.

When the stent is deployed to its expanded state, at least some segments of the struts assume an orientation transverse to the longitudinal axis, whereby to maintain a more rigid mechanical scaffolding of the stent circumferentially, to adapt the stent to maintain the patency of the vessel, duct or tract at the target site. When the stent is in its compressed state, the upper and lower curves of each opening tend toward nesting together.

Although a preferred embodiment and method of the invention have been shown and described as indicative of the best mode presently contemplated of practicing the invention, along with certain alternative embodiments, it will be apparent to those skilled in the art from a consideration of the foregoing detailed description that variations and modifications of the described embodiment and method may be made without departing from the true spirit and scope of the invention. It is therefore intended that the invention shall be limited only by the following claims and the rules and principles of applicable law.

What is claimed is:

1. A vascular or endoluminal stent comprising a biocompatible hollow tube having a longitudinal axis and open ends, a multiplicity of openings through the wall of the tube between said ends, said stent having a production state, a second state in which the stent is radially compressed and a third state in which the stent is radially expanded relative to said production state, the stent being adapted for deployment to said expanded state in a vessel, duct or tract of a patient, said multiplicity of openings through the wall of the tube being defined when the stent is in said production state by a network of tangentially interconnected, solely curvilinear struts, each of said struts running longitudinally from end to end of said tube in repetitively alternating crests and valleys without sharp breaks or angularity.

2. The stent of claim 1, wherein each of said openings is bounded circumferentially on said tube by an upper curve and a lower curve connected to form a closed curve, one of said upper and lower curves having a tighter curvature than the other of said upper and lower curves.

3. The stent of claim 2, wherein each of said openings has a shape resembling the outline of a ram's head with horns projecting outwardly and upwardly at sides of the head.

4. The stent of claim 3, wherein each of said upper and lower curves of each of said openings has a single valley.

5. The stent of claim 2, wherein each of said openings has a shape resembling the outline of a handlebar moustache.

6. The stent of claim 5, wherein each of said upper and lower curves of each of said openings has a single crest.

7. The stent of claim 1, wherein no segment of any of said struts is oriented in a direction substantially perpendicular to said longitudinal axis when the stent is in either said production state or said compressed state.

8. The stent of claim 1, wherein each of said struts has at least one segment oriented in a direction substantially perpendicular to said longitudinal axis when the stent is in said expanded state.

9. A vascular or endoluminal stent comprising a biocompatible hollow tube having a longitudinal axis and open ends, a multiplicity of openings through the wall of the tube between said ends, each of said openings being bounded circumferentially on said tube by an upper curve and a lower curve connected to form a closed curve, one of said upper and lower curves having a tighter curvature than the other of said upper and lower curves; said stent having a production state, a second state in which the stent is radially compressed and a third state in which the stent is radially expanded relative to said production state; the stent being adapted for deployment to said expanded state in a vessel, duct or tract of a patient; said multiplicity of openings through the wall of the tube being defined when the stent is in said production state by a network of tangentially interconnected, solely curvilinear struts, each of said struts running longitudinally from end to end of said tube in repetitively alternating crests and valleys without sharp breaks or angularity; said tube being longitudinally flexible to undergo a bend in the stent defining an inner arc and an outer arc, wherein the openings closest to said inner arc have upper and lower curves closer together than the upper and lower curves of circumferentially aligned openings closest to said outer arc.

10. The stent of claim 9, wherein the stent is composed of a material such that said circumferentially aligned openings in the tube wall from said inner arc to said outer arc undergo recovery toward their respective original configurations upon straightening of said bend, when the bend has occurred with the stent in either said production state or said compressed state.

11. The stent of claim 9, wherein the stent is composed of a material such that said circumferentially aligned openings in the tube wall from said inner arc to said outer arc remain in respective configurations of upper and lower curves being closer together or further apart according to their closeness to said inner arc or said outer arc, respectively, when the bend has occurred with the stent in said expanded state.

12. The stent of claim 1, wherein, when the stent is deployed to said expanded state, at least some segments of said struts assume an orientation transverse to said longitudinal axis, whereby to maintain a more rigid mechanical scaffolding of the stent circumferentially, to adapt the stent to maintain the patency of the vessel, duct or tract at a target site thereof.

13. The stent of claim 2, wherein, when the stent is in said compressed state, the upper and lower curves of each opening tend toward nesting together.

14. A multicellular stent comprising a substantially cylindrical open-ended metallic element having a longitudinal axis and a self-supporting latticework sidewall, said sidewall including a multiplicity of cells in the form of openings of substantially common size and shape separated from one another by narrow curved strips extending in a predominantly longitudinal direction, each of said cells having at least slightly different upper and lower curvatures of their respective strip boundaries to accommodate longitudinal bending of the stent, wherein each of said cells in the vicinity of the inner arc of a bend in the stent compress from said common size to a smaller size with the curved strip boundaries thereof tending toward nesting together, while each of said cells in the vicinity of the outer arc of the bend expand from said common size to a larger size, to facilitate said longitudinal bending.

15. The stent of claim 14, wherein said strips are patterned in the form of circumferentially-repeating wavelets extending continuously longitudinally from end to end of said element in alternating higher and lower crests connected tangentially to respective alternating lower and higher crests of adjacent wavelets, to facilitate relatively low friction longitudinal movement of the stent through a vessel, duct or tract of a patient's body.

16. The stent of claim 14, wherein the stent has a radially compressed state of the cylindrical element for traversing a vessel, duct or tract of a patient's body to a deployment site therein, and a radially expanded state of deployment of the cylindrical element, and none of said strips is oriented in a plane perpendicular to the longitudinal axis of the cylindrical element when the stent is in its radially compressed state.

17. The stent of claim 14, wherein each of said strips has at least one segment oriented in a plane substantially perpendicular to the longitudinal axis of the cylindrical element when the stent is in its radially expanded state, whereby to resist inwardly directed radial forces with greater rigidity than when the stent is in its radially compressed state.

18. A vascular or endoluminal stent having a compressed state and an expanded state, comprising a biocompatible hollow tube having open ends, a multiplicity of cell openings through the wall of the tube between said ends to enable said tube to be deployed by radial pressure exerted from within the tube to place the stent in said expanded state in a vessel, duct or tract of a patient, said cell openings being defined in said compressed state by a network of tangentially interconnected solely curvilinear struts, each of said struts extending longitudinally from end to end of the tube in a continuously repeating pattern of alternating high and low crests interconnected tangentially and alternately to low and high crests, respectively, of adjacent ones of said curvilinear struts at circumferentially opposite sides of the respective curvilinear strut, for low friction travel of the stent through the vessel, duct or tract.

19. A stent for traversing the lumen of a vessel, duct or tract of a patient and for deployment at a preselected site therein, comprising a biocompatible tubular member having a longitudinal axis and open ends, a multiplicity of cells arranged in a recurring pattern throughout said tubular member, each cell constituting an aperture in the wall of said tubular member, a plurality of curvilinear struts formed by narrow strips of said wall separating said cells from one another, each of said strips running the length of said tubular member in a continuously curvilinear manner without discontinuities, said strips having a sequence of tangentially interconnected crests that define the shape of said cells.

20. The stent of claim 19, wherein said sequence of tangentially interconnected crests alternates between circumferentially lower and higher crests in progression along the length of said tubular member, with tangential interconnection thereof to respectively higher and lower crests of corresponding adjacent ones of said sequences about the circumference of said tubular member.

21. The stent of claim 20, wherein said cells are of substantially uniform size and shape throughout said tubular member when the tubular member is in a substantially straight longitudinal condition.

22. A stent for traversing the lumen of a vessel, duct or tract of a patient and for deployment at a preselected site therein, comprising a biocompatible tubular member having a longitudinal axis and open ends; a multiplicity of cells arranged in a recurring pattern throughout said tubular member, each cell constituting an aperture in the wall of said tubular member and said cells being of substantially uniform size and shape throughout said tubular member when the tubular member is in a substantially straight longitudinal condition; a plurality of curvilinear struts formed by narrow strips of said wall separating said cells from one another, each of said strips running the length of said tubular member in a continuously curvilinear manner without discontinuities, said strips having a sequence of tangentially interconnected crests that define the shape of said cells and alternate between circumferentially lower and higher crests in progression along the length of said tubular member, with tangential interconnection thereof to respectively higher and lower crests of corresponding adjacent ones of said sequences about the circumference of said tubular member; said tubular member being adapted to undergo longitudinal bending during said traversal, whereupon cells in the vicinity of the bend undergo a change in size, with circumferentially adjacent crests of the respective cell tending toward close nesting at the inner curvature of the bend and toward increased separation at the outer curvature of the bend, and return to said substantially uniform size when said tube is straightened from said longitudinal bending.

23. The stent of claim 20, wherein said cells are substantially symmetrical throughout said tubular member when the tubular member has a straight longitudinal axis.

24. A stent for traversing the lumen of a vessel, duct or tract of a patient and for deployment at a preselected site therein, comprising a biocompatible tubular member having a longitudinal axis and open ends; a multiplicity of cells arranged in a recurring pattern throughout said tubular member, each cell constituting an aperture in the wall of said tubular member, said cells being substantially symmetrical throughout said tubular member when the tubular member has a straight longitudinal axis, and when said tubular member is bent to have a curved longitudinal axis, cells in the vicinity of the bend undergoing transition to an asymmetrical configuration without plastic deformation, thereby rendering said tubular member longitudinally flexible; a plurality of curvilinear struts formed by narrow strips of said wall separating said cells from one another, each of said strips running the length of said tubular member in a continuously curvilinear manner without discontinuities, said strips having a sequence of tangentially interconnected crests that define the shape of said cells and alternate between circumferentially lower and higher crests in progression along the length of said tubular member, with tangential interconnection thereof to respectively higher and lower crests of corresponding adjacent ones of said sequences about the circumference of said tubular member.

25. A vascular or endoluminal stent of low surface friction for navigating a vessel, duct or tract of a patient, said stent comprising a tubular element of biocompatible material having a longitudinal axis, open ends and a multiplicity of openings of substantially common shape and size through its wall throughout its length; said openings being bounded by a network of tangentially interconnected, continuous, predominantly longitudinally oriented curvilinear struts, without discontinuity, forming a sidewall of said tubular element; said stent adapted to be deployed by exertion of outward radial pressure on said tubular element, and when deployed, at least a segment of each strut undergoing a transition to a predominantly transverse orientation relative to said longitudinal axis.

* * * * *